United States Patent [19]

Issler et al.

[11] Patent Number: 4,731,448

[45] Date of Patent: Mar. 15, 1988

[54] PROCESS FOR THE PREPARATION OF 1-(2-HYDROXYETHYL)-2,2,6,6-TETRAMETHYL-4-PIPERIDINOL

[75] Inventors: Heinz Issler, Bensheim; Siegfried Kintopf, Bensheim/Bergstrasse; Lutz König, Worms; Hans Stephan, Bensheim, all of Fed. Rep. of Germany

[73] Assignee: Ciba-Geigy Corporation, Ardsley, N.Y.

[21] Appl. No.: 937,600

[22] Filed: Dec. 3, 1986

[30] Foreign Application Priority Data

Dec. 6, 1985 [CH] Switzerland .................... 5226/85

[51] Int. Cl.$^4$ .................................... C07D 211/46
[52] U.S. Cl. ............................... 546/248; 546/242
[58] Field of Search ........................... 546/242, 248

[56] References Cited

U.S. PATENT DOCUMENTS

| | | | |
|---|---|---|---|
| 3,974,127 | 8/1976 | Tanikella et al. | 546/248 X |
| 4,001,190 | 1/1977 | Tanikella et al. | 260/75 N |
| 4,014,887 | 3/1977 | Randell et al. | 546/248 X |
| 4,223,138 | 9/1980 | Schubart | 546/248 X |
| 4,263,202 | 4/1981 | Rasberger et al. | 546/207 X |
| 4,496,732 | 1/1985 | Lee et al. | 546/216 |

FOREIGN PATENT DOCUMENTS

| | | |
|---|---|---|
| 2656764 | 7/1977 | Fed. Rep. of Germany . |
| 2656765 | 7/1977 | Fed. Rep. of Germany . |
| 57-21368 | 2/1982 | Japan . |
| 602644 | 7/1978 | Switzerland . |

*Primary Examiner*—Joseph Paul Brust
*Attorney, Agent, or Firm*—Harry Falber

[57] ABSTRACT

There is disclosed a process for the preparation of 1-(2-hydroxyethyl-2,2,6,6-tetramethyl-4-piperidinol from triacetoneamine, which comprises first reducing triacetoneamine in water and/or a polar organic solvent by catalytic hydrogenation to 2,2,6,6-tetramethyl-4-piperidinol, and adding a catalytic amount of acid to the resultant solution, without isolation of the intermediate, after optional concentration of the solution by distillation, and subsequently reacting the 2,2,6,6-tetramethyl-4-piperidinol with ethylene oxide.

1-(2-Hydroxyethyl)-2,2,6,6-tetramethyl-4-piperidinol is a useful light and heat stabilizer for plastics and is, in addition, a valuable intermediate for the synthesis of further light stabilizer additives.

15 Claims, No Drawings

PROCESS FOR THE PREPARATION OF 1-(2-HYDROXYETHYL)-2,2,6,6-TETRAMETHYL-4-PIPERIDINOL

The present invention relates to a process for the preparation of 1-(2-hydroxyethyl)-2,2,6-6-tetramethyl-4-piperidinol by catalytic reduction of 4-oxo-2,2,6,6-tetramethylpiperidine, also known as triacetoneamine, and subsequent reaction of the resultant 2,2,6,6tetramethyl-4-piperidinol with ethylene oxide.

1-(2-Hydroxyethyl)-2,2,6,6-tetramethyl-4-piperidinol is a useful light and heat stabiliser for plastics and, in addition, is a valuable intermediate for the synthesis of light stabilizer additives.

The synthesis of 1-(2-hydroxyethyl)-2,2,6,6-tetramethyl-4-piperidinol is generally carried out, starting from triacetoneamine, in two steps, wherein triacetoneamine is first reduced by catalytic hydrogenation to 2,2,6,6-tetramethyl-4-piperidinol, e.g. as described in CH-A No. 602 644. The further reaction of 2,2,6,6-tetramethyl-4-piperidinol to 1-(2-hydroxyethyl)-2,2,6,6-tetramethyl-4-piperidinol is known e.g. from the process described in JP-A No. 57-21368, wherein a large and not at all desirable excess of ethylene oxide is used. The synthesis of 1-(2-hydroxyethyl)-2,2,6,6-tetramethyl-4-piperidinol from 2,2,6,6-tetramethyl-4-piperidinol and ethylene oxide in the presence of a strongly basic catalyst is disclosed e.g. in U.S. Pat. No. 3,974,127 and 4,001,190, but the temperature conditions employed in the process are complicated and unsuitable for carrying out the synthesis on an industrial scale.

The principal drawback of the known synthesis for obtaining 1-(2-hydroxyethyl)-2,2,6,6-tetramethyl-4-piperidinol resides in the fact that the intermediate, 2,2,6,6-tetramethyl-4-piperidinol, has in principle up to now had to be isolated and/or purified before the further reaction, e.g. by salting out or recrystallisation, if the final product is to be obtained in an acceptable yield. The isolation of the intermediate, however, entails losses in yield, is time-consuming, and results in environmental pollution.

It has now been found that 1-(2-hydroxyethyl)-2,2,6,6-tetramethyl-4-piperidinol can be obtained from triacetoneamine without the shortcomings referred to above, especially without isolation of the intermediate, 2,2,6,6-tetramethyl-4-piperidinol, by adding a catalytic amount of acid to the solution of 2,2,6,6-tetramethyl-4-piperidinol resulting from the catalytic hydrogenation before the further reaction and, in an optional step, concentrating said solution by distillation.

Accordingly, the invention relates to a process for the preparation of 1-(2-hydroxyethyl)-2,2,6,6-tetramethyl-4-piperidinol from triacetoneamine, which comprises reducing triacetoneamine in a manner known per se by catalytic hydrogenation in water or in a polar organic solvent or in a mixture thereof with water, to give 2,2,6,6-tetramethyl-4-piperidinol, adding a catalytic amount of an inorganic or organic acid to the solution of 2,2,6,6-tetramethyl-4-piperidinol as obtained or after concentrating the solution by distillation, without further purification and/or isolation of the intermediate, with the proviso that, if the solution of the intermediate is concentrated, the addition of acid is made before or after the distillation, and that the concentrated solution or melt may be diluted again with the same solvent or with another solvent, and subsequently reacting said solution or melt of 2,2,6,6-tetramethyl-4-piperidinol with ethylene oxide in a molar excess of 1–35% in the temperature range from 60°–170° C.

The first step (catalytic hydrogenation of triacetoneamine) is carried out in aqueous solution in a polar organic solvent or in a mixture thereof with water. If a polar organic solvent is employed, then it is preferably one that is miscible with water. Examples of such solvents are monohydric or polyhydric $C_1$–$C_5$ alcohols or ether alcohols such as monohydric $C_1$–$C_5$ alcohols, glycols and glycol ethers. Representative examples are: methanol, ethanol, isopropanol, n-propanol, butanol, ethylene glycol, ethylene glycol ethers and the like. One embodiment of the process comprises e.g. using a polar organic solvent as cited above, and another comprises using a mixture thereof with water. It is preferred, however, to carry out the catalytic hydrogenation of triacetoneamine in aqueous solution.

A further embodiment of the process of this invention comprises using a non-polar solvent in addition to a solvent as cited above (including water). Typical examples of such solvents are aliphatic or aromatic hydrocarbons, e.g. benzene, toluene, xylene and the like.

The hydrogenation can be carried out in a manner known per se using a conventional hydrogenation catalyst, preferably a noble metal catalyst. Representative examples of such catalysts are in particular Raney nickel and, most preferably, ruthenium on carbon. It is preferred to carry out the hydrogenation in the manner described in CH-A No. 602 644.

The solution of 2,2,6,6-tetramethyl-4-piperidinol obtained after the hydrogenation can be further used direct, i.e. after addition of acid it is reacted with ethylene oxide. However, it is often expedient to reduce the volume of the solution before further processing. This is done by distillation under normal or reduced pressure. Accordingly, one embodiment of the process of this invention comprises distilling the solution of 2,2,6,6-tetramethyl-4-piperidinol to a concentration of at least 30 % (e.g. 30 to 60%), preferably at least 50%, of 2,2,6,6-tetramethyl-4-piperidinol. For example, the solution is distilled to a 70% or 80% concentration of 2,2,6,6,-tetramethyl-4-piperidinol. Very good results are also obtained by continuing the distillation up to a 90% concentration of 2,2,6,6-tetramethyl-4-piperidinol or until a melt of is obtained, i.e. removing virtually the entire solvent by distillation. This concentration, however, does not mean isolation of the 2,2,6,6-tetramethyl-4-hydroxypiperidine, as the solvent cannot be completely removed in this manner and by-products are also still present in the melt.

If distillation is carried out, the solution of 2,2,6,6-tetramethyl-4-piperidinol is distilled under normal pressure or, preferably, under a reduced pressure of 100 to 900 mbar, in particular of 100 to 300 mbar. Depending on the pressure, distillation at a temperature in the range from 30° to 100° C. affords a two-phase mixture consisting of an aqueous and an oily phase, which is discarded.

If the solution of 2,2,6,6-tetramethyl-4-piperidinol is distilled, the addition of acid may in principle be made before or after the distillation. It is preferred, however, to add the acid after the distillation to the remaining solution or melt of the intermediate.

If the solution resulting from the hydrogenation step is distilled, the residual concentrated solution or melt can be diluted again before further processing, using the same solvent or another one. It is possible to use e.g. a solvent as indicated for the hydrogenation step (including water and the optional concurrently used non-polar solvent). The choice of solvent can depend on the manner in which it is desired to isolate the 1-(2-hydroxyethyl)-2,2,6,6-tetramethyl-4-piperidinol obtained as final product or on whether it is desired to obtain it direct for possible further processing in the requisite solvent.

The acid to be added in catalytic amount can be any, preferably protic, inorganic or organic acid. Representative examples of such acids are inorganic acids such as HCl HBr, $H_2SO_4$, $H_3PO_4$, $H_2SO_3$ and $HNO_3$, and organic aromatic or aliphatic carboxylic acids such as formic acid, acetic acid, haloacetic acids, propionic acid, benzoic acid and substituted benzoic acids, as well as aromatic sulfonic acids such as benzenesulfonic acid and substituted benzenesulfonic acids, e.g. p-toluenesulfonic acid. It is preferred to use HCl, formic acid, acetic acid, p-toluenesulfonic acid and, most preferably, $H_2SO_4$.

The inorganic or organic acid is preferably employed in an amount of 0.1 to 10%, e.g. 0.1 to 5%, in particular 0.3 to 3% and, most preferably, 0.5 to 1%, based on the optionally concentrated and optionally once more diluted solution or melt of 2,2,6,6-tetramethyl-4-piperidinol.

As catalytic amount of acid, it is preferred to use 0.5 to 1.0% of $H_2SO_4$, based on the optionally concentrated solution or melt of 2,2,6,6-tetramethyl-4-piperidinol.

The ethylene oxide is added in a molar excess of 1 to 35%, e.g. 10 to 35%, based on the 2,2,6,6-tetramethyl-4-piperidinol present in solution. The addition of ethylene oxide to the reaction solution is preferably made over 1 to 120 minutes and, most preferably, over 1 to 40 minutes, e.g. over 1 to 10 minutes.

The reaction with ethylene oxide takes place in the temperature range from 60°–170° C., e.g. from 60°–120° C. It is convenient to carry out the reaction in an autoclave. The ethylene oxide is preferably added at a specific temperature and the reaction proceeds without external cooling or heating ("quasi-adiabatic reaction"). For example, the ethylene oxide is added in the temperature range from 80°–100° C., whereupon he temperature usually rises, e.g. to about 120° C. However, the temperature may also fall. It is on occasion expedient to carry out further reaction with optional heating. When the reaction is complete, the reaction mixture can be worked up in conventional manner. Thus by cooling or addition of suitable precipitants, the final product can be precipitated isolated by filtration, washed and recrystallized. For further processing, the solution can also be used direct.

The process of this invention for the preparation of 1-(2-hydroxyethyl)-2,2,6, 6-tetramethyl-4-piperidinol from triacetoneamine can be carried out discontinously (batchwise) or continuously, e.g. in a rotating disc reactor or in a reactor cascade. A continuous reaction is preferred.

In a preferred embodiment of the process of the invention, the catalytic hydrogenation of triacetoneamine is carried out in aqueous solution and the reaction solution, after optional distillation to obtain a concentration of 2,2,6,6-tetramethyl-4-piperidinol of up to 70%, is reacted with ethylene oxide at 60°–120° C. under quasi adiabatic conditions, using a molar excess of 10–35% of ethylene oxide, and the resultant product is isolated and worked up in known manner.

Conventional analytical methods may be employed to determine the concentration of 2,2,6,6-tetramethyl-4-piperidinol (intermediate solution) and 1-(2-hydroxyethyl)-2,2,6,6-tetramethyl-4-piperidinol (where obtained as solution of final product), with the concentration preferably being determined by gas chromatography.

By means of the process of this invention it is possible to obtain 1-(2-hydroxyethyl)-2,2,6,6-tetramethyl-4-piperidinol from triacetoneamine in high yield without isolation of 2,2,6,6-tetramethyl-4-piperidinol. The process is simple to perform, time-saving and also environmentally safe, as the salts and solvent residues resulting from the salting out and recrystallisation operations employed hitherto are avoided.

The following Examples illustrate the invention in more detail. Throughout the entire description and claims of this specification, parts and percentages are by weight unless otherwise stated. The concentration of 2,2,6,6-tetramethyl-4-piperidinol and 1-(2-hydroxyethyl)-2,2,6,6-tetramethyl-4-piperidinol in the Examples is determined by gas chromatography.

EXAMPLE 1

1800 kg of distilled triacetoneamine (92–98% pure) are diluted with 2200 liters of water and hydrogenated at 70°–80° C. and under a hydrogen pressure of 10 bar in the presence of ruthenium on carbon. The catalyst is thereafter removed by filtration and the solution of 2,2,6,6-tetramethyl-4-piperidinol is stored in a tank before further processing.

Concentration of 2,2,6,6-tetramethyl-4-piperidinol in the solution: 40%. Yield: 91–97%.

EXAMPLE 2

595 g of the 2,2,6,6-tetramethyl-4-piperidinol solution obtained in Example 1 and 11 g of $H_2SO_4$ (96%) are charged to an autoclave and 93 g of ethylene oxide are rapidly added, whereupon the temperature rises to c. 117° C. (quasi-adiabatic reaction conditions). After a total reaction time of 3 hours, the reaction mixture is discharged hot and cooled to 20° C. with stirring. The crystals of 1-(2-hydroxyethyl)-2,2,6,6-tetramethyl-4-piperidinol are filtered with suction and washed with water and toluene. Melting point: 180°–182° C. Yield: 86%.

The mother liquor contains further 1-(2-hydroxyethyl)-2,2,6,6-tetramethyl-4-piperidino which, after working up, increases the yield to 90%.

EXAMPLE 3

571 g of the 2,2,6,6-tetramethyl-4-piperidinol solution obtained in Example 1 are subjected to distillation and 14.5% by weight of the solution is distilled off as an azeotrope under vacuum (500–900 mbar) at c. 60° C. Then 488 g of the distillation residue (concentration of 2,2,6,6-tetramethyl-4-piperidinol: c. 48% by weight) and 5 g of 96% $H_2SO_4$ are charged to an autoclave at 92° C. Then 88 g of ethylene oxide are added rapidly, whereupon the temperature rises to c. 117° C. (quasi-adiabatic reaction conditions). After a total reaction time of 3 hours the reaction mixture is discharged hot and cooled to 20° C. with stirring. The crystals of 1-(2-hydroxyethyl)-2,2,6,6-tetramethyl-4-piperidinol are filtered with suction and washed with water and toluene.

Melting point: 180°–182° C. Yield: 91%.

The mother liquor contains further 1-(2-hydroxyethyl)-2,2,6,6-tetramethyl-4-piperidinol which, when isolated, increases the total yield to 97%.

EXAMPLE 4

681 g of the 2,2,6,6-tetramethyl-4-piperidinol solution obtained in Example 1 are subjected to distillation and 30.8% by weight of the solution is distilled off as an azeotrope under vacuum (500–900 mbar) at c. 60° C.–80° C. Then 471 g of the distillation residue (concentration of 2,2,6,6-tetramethyl-4-piperidinol: c. 60% by weight) and 3 g of 96% $H_2SO_4$ are charged to an autoclave at 93° C. Then 88 g of ethylene oxide are added rapidly, whereupon the temperature rises to c. 119° C. (quasi-adiabatic reaction conditions). After a total reaction time of 3 hours the reaction mixture is discharged hot and cooled to 20° C. with stirring. The crystals of 1-(2-hydroxyethyl)-2,2,6,6-tetramethyl-4-piperidinol are filtered with suction and washed with water and toluene.

Melting point: 180°–182° C. Yield: 92.5%.

The mother liquor contains further 1-(2-hydroxyethyl)-2,2,6,6-tetramethyl-4-piperidinol which, when isolated, increases the total yield to 95.3%.

EXAMPLE 5

1663 g of the 2,2,6,6-tetramethyl-4-piperidinol solution obtained in Example 1 are subjected to distillation and 49.4% by weight of the solution is distilled off as an azeotrope under vacuum (500–900 mbar) at c. 60° C.–80° C. Then 841 g of the distillation residue (concentration of 2,2,6,6-tetramethyl-4-piperidinol: c. 80% by weight) and 4.3 g of 96% $H_2SO_4$ are charged to an autoclave at 93° C. Then 205 g of ethylene oxide are added rapidly, whereupon the temperature rises to c. 138° C. (quasi-adiabatic reaction conditions). After a total reaction time of 3 hours the reaction mixture is discharged hot and cooled to 20° C. with stirring. The crystals (1-(2-hydroxyethyl)-2,2,6,6-tetramethyl-4-piperdinol) are filtered with suction and washed with water and toluene.

Melting point: 180°–182° C. Yield: 93.5%.

The mother liquor contains further 1-(2-hydroxyethyl)-2,2,6,6-tetramethyl-4-piperidinol which, when isolated, increases the total yield to 95%.

EXAMPLE 6

1577 g of the 2,2,6,6-tetramethyl-4-piperidinol solution obtained in Example 1 are concentrated to a melt by distillation at 80°–150° C. The distillation residue and 9.5 g of 96% $H_2SO_4$ are charged to an autoclave at 139° C. Then 195 g of ethylene oxide are added rapidly, whereupon the temperature rises to c. 165° C. (quasi-adiabatic reaction conditions). After a total reaction time of 3 hours the reaction mixture is discharged hot and cooled to 20° C. with stirring. The crystals of 1-(2-hydroxyethyl-2,2,6,6-tetramethyl-4-piperidinol are filtered with suction and washed with water and toluene.

Melting point: 180°–182° C. Yield: 98.3%.

The mother liquor contains further 1-(2-hydroxyethyl)-2,2,6,6-tetramethyl-4-piperidinol which, when isolated, increases the total yield to 99.4%.

EXAMPLE 7

579 g of the 2,2,6,6-tetramethyl-4-piperidinol solution obtained in Example 1 are subjected to distillation and 10% by weight of the solution is distilled off as an azeotrope under vacuum (500–900 mbar) at c. 60° C.–80° C. The distillation residue and 5 g of 36% HCl are charged to an autoclave at 90° C. Then 89 g of ethylene oxide are added rapidly, whereupon the temperature rises to c. 110° C. After a total reaction time of 3 hours the reaction mixture is discharged hot and cooled to 20° C. with stirring. The crystals of 1-(2-hydroxyethyl)-2,2,6,6-tetramethyl-4-piperidinol are filtered with suction and washed with water and toluene.

Melting point: 180°–182° C. Yield: 90.8%.

The mother liquor contains further 1-(2-hydroxyethyl)-2,2,6,6-tetramethyl-4-piperidinol which, when isolated, increases the total yield to 93.6%.

EXAMPLE 8

609 g of the 2,2,6,6-tetramethyl-4-piperidinol solution obtained in Example 1 are subjected to distillation and 10% by weight of the solution is distilled off as an azeotrope under vacuum (500–900 mbar) at c. 60° C.–80° C. The distillation residue and 10 g of glacial acetic acid are charged to an autoclave at 90° C. Then 94 g of ethylene oxide are added rapidly, whereupon the temperature rises to c. 110° C. After a total reaction time of 3 hours the reaction mixture is discharged hot and cooled to 20° C. with stirring. The crystals of 1-(2-hydroxyethyl)-2,2,6,6-tetramethyl-4-piperidinol are filtered with suction and washed with water and toluene.

Melting point: 180°–182° C. Yield: 81.6%.

The mother liquor contains further 1-(2-hydroxyethyl)-2,2,6,6-tetramethyl-4-piperidinol which, when isolated, increases the total yield to 85.2%.

EXAMPLE 9

627 gm of the 2,2,6,6-tetramethyl-4-piperidinol solution obtained in Example 1 are subjected to distillation and 10% by weight of the solution is distilled off as an azeotrope under vacuum (500–900 mbar) at c. 60° C.–80° C. The distillation residue and 2.5 g of 100% formic acid are charged to an autoclave at 90° C. Then 92 g of ethylene oxide are added rapidly, whereupon the temperature rises to c. 110° C. After a total reaction time of 3 hours the reaction mixture is discharged hot and cooled to 20° C. with stirring. The crystals of 1-(2-hydroxyethyl)-2,2,6,6-tetramethyl-4-pyridinol are filtered with suction and washed with water and toluene.

Melting point: 180°–182° C. Yield: 86.3%.

The mother liquor contains further 1-(2-hydroxyethyl)-2,2,6,6-tetramethyl-4-piperidinol which, when isolated, increases the total yield to 86.3%.

EXAMPLE 10

644 g of the 2,2,6,6-tetramethyl-4-piperidinol solution obtained in Example 1 are subjected to distillation and 10% by weight of the solution is distilled off as an azeotrope under vacuum (500–900 mbar) at c. 60° C.–80° C. The distillation residue and 10.6 g of p-toluenesulfonic acid monohydrate are charged to an autoclave at 90° C. Then 94 g of ethylene oxide are added rapidly, whereupon the temperature rises to c. 110° C. After a total reaction time of 3 hours the reaction mixture is discharged hot and cooled to 20° C. with stirring. The crystals of 1-(2-hydroxyethyl)-2,2,6,6-tetramethyl-4-piperidinol are filtered with suction and washed with water and toluene.

Melting point: 180°–182° C. Yield: 90.1%.

The mother liquor contains further 1-(2-hydroxyethyl)-2,2,6,6-tetramethyl-4-piperidinol which, when isolated, increases the total yield to 92.8%.

EXAMPLE 11

616 g of the 2,2,6,6-tetramethyl-4-piperidinol solution obtained in Example 1 are concentrated to a melt by distillation at 80°–150° C. The distillation residue is diluted with 353 g of butyl acetate and, after addition of 5.0 g of 96% of $H_2SO_4$, charged to an autoclave at 96°

C. Then 90 g of ethylene oxide are added rapidly, whereupon the temperature falls to 90° C. After a total reaction time of 4.7 hours (100° C.) the reaction mixture containing 1-(2-hydroxyethyl)-2,2,6,6-tetramethyl-4-piperidinol is discharged hot and completely concentrated by distillation.

EXAMPLE 12

511 g of the 2,2,6,6-tetramethyl-4-piperidinol solution obtained in Example 1 are concentrated to a melt by distillation at 80°–150° C. The distillation residue is diluted with 307 g of toluene and, after addition of 5.0 g of 96% of $H_2SO_4$, charged to an autoclave at 96° C. Then 90 g of ethylene oixide are added rapidly, whereupon the temperature falls to 138° C. After a total reaction time of 4.3 hours at 140°–150° C., the reaction mixture containing 1-(2-hydroxyethyl)-2,2,6,6-tetramethyl-4-piperidinol is cooled to 105° C., then discharged and completely concentrated by distillation.

EXAMPLE 13

580 g of the 2,2,6,6-tetramethyl-4-piperidinol solution obtained in Example 1 are subjected to distillation and 10% by weight of the solution is distilled off as an azeotrope under vacuum (500–900 mbar) and c. 60°–80° C. The distillation residue, 26 g of toluene and 3.5 g of 96% $H_2SO_4$ are charged to an autoclave at 90° C. Then 89 g of ethylene oxide are added rapidly, whereupon the temperature rises to c. 110° C. After a total reaction time of 3 hours the reaction mixture is discharged hot and cooled to 20° C. with stirring. The crystals of 1-(2-hydroxyethyl)-2,2,6,6-tetramethyl-4-piperidinol are filtered with suction and washed with water and toluene.

Melting point: 180°–182° C. Yield: 90.0%.

The mother liquor contains further 1-(2-hydroxyethyl)-2,2,6,6-tetramethyl-4-piperidinol which, when isolated, increases the total yield to 92.6%.

EXAMPLE 14

618 g of the 2,2,6,6-tetramethyl-4-piperidinol solution obtained in Example 1 are concentrated to a melt by distillation at 80°–150° C. The distillation residue is diluted with 406 g of ethylene glycol and, after addition of 3.7 g of 96% of $H_2SO_4$, charged to an autoclave at 96° C. Then 95 g of ethylene oxide are added rapidly, whereupon the temperature rises to c. 121° C. (quasi-adiabatic reaction conditions). After a total reaction time of 3 hours the reaction mixture is discharged hot and cooled with stirring to 20° C. The crystals of 1-(2-hydroxyethyl)-2,2,6,6-tetramethyl-4-piperidinol are filtered with suction and washed with water and toluene.

Melting point: 180°–182° C. Yield: 79.8%.

The mother liquor contains further 1-(2-hydroxyethyl)-2,2,6,6-tetramethyl-4-piperidinol which, when isolated, increases the total yield to 89.6%.

EXAMPLE 15

592 g of the 2,2,6,6-tetramethyl-4-piperidinol solution obtained in Example 1 are concentrated to a melt by distillation at 80°–150° C. The distillation residue is diluted with 104 g of isopropanol and 54 g of water and, after addition of 3.5 g of 96% of $H_2SO_4$, charged to an autoclave at 82° C. Then 91 g of ethylene oxide are added rapidly, whereupon the temperature rises to c. 92° C. (quasi-adiabatiuc reaction conditions). After a total reaction time of 3 hours the reaction mixture is discharged hot, concentrated by distillation, and cooled with stirring to 20° C. The crystals of 1-(2-hydroxyethyl)-2,2,6,6-tetramethyl-4-piperidinol are filtered with suction and washed with water and toluene.

Melting point: 180°–182° C. Yield 85.5%.

The mother liquor contains further 1-(2-hydroxyethyl)-2,2,6,6-tetramethyl-4-piperidinol which, when isolated, increases the total yield to 95.2%.

EXAMPLE 16

539 g of the 2,2,6,6-tetramethyl-4-piperidinol solution obtained in Example 1 are concentrated to a melt by distillation at 80°–150° C. The distillation residue is diluted with 323 g of methanol and, after addition of 3.2 g of 96% of $H_2SO_4$, charged to an autoclave at 83° C. Then 83 g of ethylene oxide are added rapidly, whereupon the temperature rises to c. 98° C. (quasi-adiabatic reaction conditions). After a total reaction time of 3 hours the reaction mixture is discharged hot, concentrated by distillation, and cooled with stirring to 20° C. The crystals of 1-(2-hydroxyethyl)-2,2,6,6-tetramethyl-4-piperidinol are filtered with suction and washed with water and toluene.

Melting point: 180°–182° C. Yield 81.5%.

The mother liquor contains further 1-(2-hydroxyethyl)-2,2,6,6-tetramethyl-4-piperidinol which, when isolated, increases the total yield to 90.0%.

EXAMPLE 17

410 g of distilled triacetoneamine (92–98% pure) are diluted with methanol and hydrogenated at 80° C. and under 40 bar hydrogen pressure in the presence of ruthenium on carbon. The catalyst is thereafter removed by filtration and the 2,2,6,6-tetramethyl-4-piperidinol solution is stored in a tank before further processing.

Concentration of 2,2,6,6-tetramethyl-4-piperidinol in the solution: c. 50%. Yield: 90–93%.

EXAMPLE 18

712 g of the 2,2,6,6-tetramethyl-4-piperidinol solution obtained in Example 17 and 5.3 g of 96% $H_2SO_4$ are charged to an autoclave at 85° C. Then 137 g of ethylene oxide are added rapidly, whereupon the temperature rises to c. 125° C. (quasi-adiabatic reaction conditions). After a total reaction time of 3 hours the reaction mixture is discharged hot, concentrated by distillation and cooled to 20° C. with stirring. The crystals of 1-(2-hydroxyethyl)-2,2,6,6-tetramethyl-4-piperdinol are filtered with suction and washed with water and toluene.

Melting point: 180°–182° C. Yield: 80.8%.

The mother liquor contains further 1-(2-hydroxyethyl)-2,2,6,6-tetramethyl-4-piperidinol which, when isolated, increases the total yield to 89.6%.

What is claimed is:

1. In the process for the preparation of 1-(2-hydroxyethyl)-2,2,6,6-tetramethyl-4-piperidinol by reducing triacetoneamine by catalytic hydrogenation in water or in a polar organic solvent, or in a mixture thereof, and subsequently reacting the resulting 2,2,6,6-tetramethyl-4-piperidinol with excess ethylene oxide, the improvements which comprise (i) adding, prior to the reaction with the ethylene oxide, a catalytic amount of an inorganic or organic acid to the solution of 2,2,6,6-tetramethyl-4-piperidinol or to said solution concentrated by distillation with the proviso that, if the solution is concentrated, the acid is added before or after distillation, (ii) adding the ethylene oxide in a molar excess of 1–35%, and (iii) maintaining the temperature of the reaction with the ethylene oxide in a range from 60° to 170° C.

2. The process of claim 1, wherein said concentrated solution is diluted with the identical solvent prior to the addition of the ethylene oxide.

3. The process of claim 1, wherein said concentrated solution is diluted with a different solvent prior to the addition of the ethylene oxide.

4. A process according to claim 1, wherein the 2,2,6,6-tetramethyl-4-piperidinol solution is further reacted without distillation.

5. A process according to claim 1, wherein the 2,2,6,6-tetramethyl-4-piperidinol solution is distilled to a concentration of up to 70% of 2,2,6,6-tetramethyl-4-piperidinol.

6. A process according to claim 1, wherein the 2,2,6,6-tetramethyl-4-piperidinol solution is distilled to a concentration of at least 30%, of 2,2,6,6-tetramethyl-4-piperidinol.

7. A process according to claim 6, wherein the 2,2,6,6-tetramethyl-4-piperidinol solution is concentrated to a melt.

8. A process according to claim 1, which comprises carrying out the catalytic hydrogenation in aqueous solution, distilling the 2,2,6,6-tetramethyl-4-piperidinol solution to a concentration of up to 70% of 2,2,6,6-tetramethyl-4-piperidinol, adding the ethylene oxide in a molar excess of 10–35% at 60°–120° C. and allowing the ethylene oxide reaction to proceed without external cooling or heating.

9. A process according to claim 5, wherein the 2,2,6,6-tetramethyl-4-piperidinol solution contains 30 to 60% of 2,2,6,6-tetramethyl-4-piperidinol before the addition of the catalytic amount of acid.

10. A process according to claim 1, wherein 0.1 to 5%, by weight, is added as the catalytic amount of acid.

11. A process according to claim 1 which is carried out continuously.

12. A process according to claim 1, wherein the polar organic solvent employed for the hydrogenation step is a monohydric or polyhydric $C_1$–$C_5$ alcohol, an ether alcohol or a mixture thereof.

13. A process according to claim 1, wherein the polar organic solvent is a monohydric $C_1$–$C_5$ alcohol, a glycol or a glycol ether.

14. A process according to claim 1, wherein a nonpolar solvent is concurrently employed in the hydrogenation step in addition to water, the polar organic solvent or the mixture thereof.

15. A process according to claim 1, wherein the addition of acid is made after distillation of the 2,2,6,6-tetramethyl-4-piperidinol solution.

* * * * *